United States Patent [19] [11] 4,135,935
Pfeil et al. [45] Jan. 23, 1979

[54] SINTERED COMPOSITE MATERIAL, A PROCESS OF MAKING SAME, AND A METHOD OF USING SAME

[75] Inventors: Emanuel Pfeil, Marburg; Heinz Broemer, Hermannstein, both of Fed. Rep. of Germany

[73] Assignee: Ernst Leitz Wetzlar GmbH, Wetzlar, Fed. Rep. of Germany

[21] Appl. No.: 764,205

[22] Filed: Jan. 31, 1977

Related U.S. Application Data

[63] Continuation of Ser. No. 506,610, Sep. 16, 1974, abandoned.

[30] Foreign Application Priority Data

Sep. 17, 1973 [DE] Fed. Rep. of Germany ....... 2346739
Feb. 4, 1974 [DE] Fed. Rep. of Germany ....... 2346739
Jul. 18, 1974 [DE] Fed. Rep. of Germany ....... 2434979

[51] Int. Cl.² .......................... C08K 3/32; C08K 3/40; C09K 3/00
[52] U.S. Cl. ........................................ 106/35; 3/1.9; 65/18; 65/33; 106/39.6; 106/45; 106/52; 106/73.1; 128/92 C
[58] Field of Search .................. 106/45, 73.1, 73.5, 106/40 R, 35; 3/1.9, 1.913; 128/92 C, 92 A; 65/33, 18

[56] References Cited

U.S. PATENT DOCUMENTS

| | | | |
|---|---|---|---|
| 2,980,998 | 4/1961 | Coleman et al. | 106/45 X |
| 3,516,810 | 6/1970 | Ivey | 65/33 |
| 3,662,405 | 5/1972 | Bortz et al. | 106/40 R |
| 3,787,900 | 1/1974 | McGee | 3/1.9 |
| 3,883,337 | 5/1975 | Helgesson et al. | 65/33 |
| 3,905,047 | 9/1975 | Long | 106/45 X |
| 3,919,723 | 11/1975 | Heimke et al. | 106/45 X |
| 3,922,155 | 11/1975 | Broemer et al. | 65/33 |
| 3,975,203 | 8/1976 | Dietz | 106/39.6 |
| 3,981,736 | 9/1976 | Broemer et al. | 106/39.6 |

OTHER PUBLICATIONS

Szustakowski, M. et al., "Structure of Apatite in Vitreous Thermophosphates", Chemia Stosowana, Series A (1970) 14(1), pp. 77–80.
Hench, L. L. et al. "Bonding Mechanisms at the Interface of Ceramic Prosthetic Materials"—J. Biomed. Material Res. Symposium (1971), No. 2—Part 1, pp. 117–141.
Hench, L. L. et al., "Direct Chemical Bond of Bio-Active Glass–Ceramic Materials to Bone and Muscle"—J. Biomed. Mat. Res. Symp. (1973) No. 4, pp. 25, 28, 29.
Thrush et al.,—"Dictionary of Mining, Mineral and Related Terms", Bureau of Mines—1968—p. 809, "Permutite".
Weyl, W. A.—"Phosphates in Ceramic Ware: I, in Opal Glasses"—J. Am. Cer. Soc. 24, (1941), pp. 221–225.
Weyl, W. A.—"Phosphates in Ceramic Ware: II, Role of Phosphorus In Bone China," J. Am. Cer. Soc. 24 (1941), pp. 245–247.

*Primary Examiner*—Helen McCarthy
*Attorney, Agent, or Firm*—Richard L. Schwaab

[57] ABSTRACT

A valuable composite material is produced by sintering together a first starting material A composed of at least one mineral component, preferably of the apatite group and a second starting material B composed of an inorganic multi-component system, such as a glass or a glass ceramic material which may contain at least one modifier. The modifier may be an agent causing under the sintering conditions foaming of the composite material, such as a carbonate, or it may be a radioactive agent. The first starting material may also contain an inorganic permutite serving as ion exchange agent. The composite material is useful as implant material in the animal and human body for replacing damaged bones or teeth, as a radioactive source, for instance, for exposing the body to radioactive irradiation, as an ion donor, for instance, for supplying the body with calcium, magnesium, and/or potassium ions, as a filter material for removing harmful agents from the body, and for other purposes.

2 Claims, 1 Drawing Figure

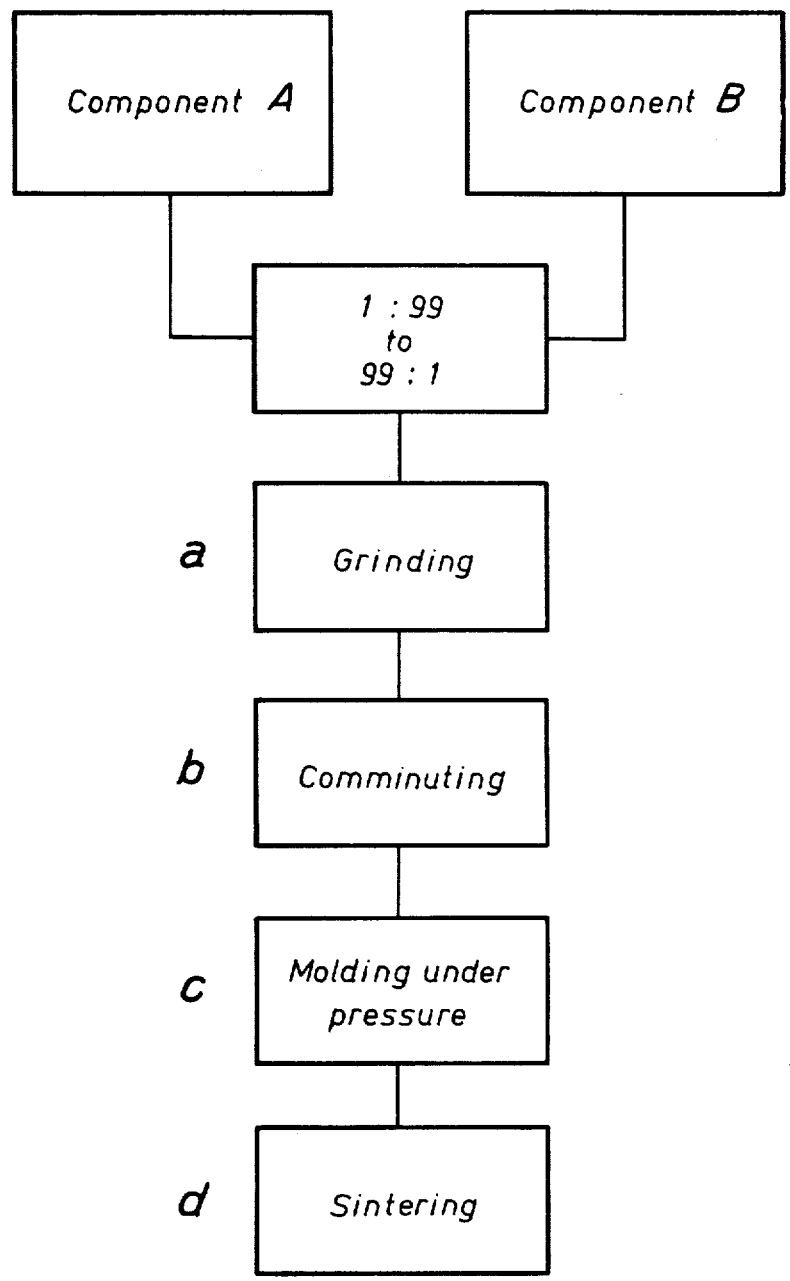

SINTERED COMPOSITE MATERIAL, A PROCESS OF MAKING SAME, AND A METHOD OF USING SAME

CROSS-REFERENCE TO RELATED APPLICATION

This is a continuation, of application Ser. No. 506,610, filed Sept. 16, 1974, now abandoned.

The present application is related to copending applications Ser. No. 471,891 of HEINZ BROEMER, HANS-HERBERT KAES, and EMANUAL PFEIL, filed May 21, 1974, and entitled "GLASS CERAMIC MATERIAL AND PROCESS OF MAKING AND USING SAME", now U.S. Pat. No. 3,922,155, and Ser. No. 471,976 of HANS-HERBERT KAES, filed May 21, 1974, and entitled "GLASS CERAMIC MATERIAL OF HIGH MECHANICAL STRENGTH AND PROCESS OF MAKING SAME," now abandoned, which applications are incorporated by reference into the present specification.

BACKGROUND OF THE INVENTION (1) Field of the Invention

The present invention relates to the manufacture of a composite or compound material and more particularly to a simple and highly advantageous sintering process for producing a glass-ceramic composite material, to such a composite material, and to the method of using it more particularly in medico-engineering, such as for osteosynthesis.

(2) Description of the Prior Art

It is known that glass-ceramic materials which contain apatite crystallites can be used as bone replacement materials. However, such a glass-ceramic material has the disadvantage that it must be manufactured via a melt. Furthermore, useful glass ceramics for said special purpose of use are obtained only by starting with certain exactly defined components of the starting mixture in exactly predetermined amounts thereof.

SUMMARY OF THE INVENTION

It is one object of the present invention to provide a simple and highly advantageous sintering process which does not have the disadvantages of the heretofore used melting process and by which a composite or compound material having the structure of apatite-containing glass ceramics is produced.

Another object of the present invention is to provide such a sinter-produced composite material.

A further object of the present invention is to provide a method of using such a sinter-produced composite material especially in the medico-engineering field, for instance, for replacing bones and teeth (osteosynthesis) and for other purposes.

Other objects of the present invention and advantageous features thereof will become apparent as the description proceeds.

These objects are achieved according to the present invention by carrying out the sintering process as follows:

A first starting material A comprising at least one mineral component is sintered together with a second starting material B consisting of an inorganic multi-component or complex system. In this connection it can be advantageous to grind and mix the two starting materials A and B before they are sintered together. The mineral component of the starting material A may be a natural or synthetic mineral of the apatite group $(Ca_5[(F, Cl, OH)(PO_4)_3])$. It is also possible to use an apatite prepared by precipitation and having a disturbed crystal lattice structure.

The inorganic multi-component system of the starting material B can be a glass, a mixture of components which can be fused together to form a glass, a glass-ceramic material, or a mixture of components which can be fused together to form a glass-ceramic material.

Preferably the mixture consisting of said two starting materials A and B additionally contains at least one modifier. Such a modifier affects, i.e., modifies in a predetermined manner the properties of the resulting composite material, for instance, by loosening up its structure or by inflating or expanding the same. Compounds which are capable of releasing gases under the temperature-time adjusted sintering conditions, i.e., under the respective "sintering timetable," can be used as modifiers. Preferred modifiers are the carbonates of the alkali metals and alkaline earth metals, especially calcium carbonate $(CaCO_3)$. The nitrates and hydrogen carbonates of the alkali metals or alkaline earth metals can also be added as modifiers; likewise, although less advantageously, the sulfates of such metals of the first and second group of the Periodic System. Not only a single modifier can be added to the starting materials A and B but also a mixture thereof. Addition of such modifiers results in a permanent formation of gas bubbles under the specific temperature-time conditions of the sintering process. The gas bubbles cannot escape from the resulting sintered composite material due to its viscosity. Thus the final composite material is highly porous, i.e., its specific surface is very considerably enlarged.

Radioactive compounds such as potassium carbonate with the radioactive isotope $^{41}K$ can also be added as modifiers.

It is also possible to replace the mineral component forming the first starting material A in whole or in part by another or additional mineral component. For instance, such other additional mineral component may be a mineral of the permutite group, such as a permutite of the formula $Na[AlSiO_4].H_2O$.

The sintering process of the present invention permits to produce composite materials of any desired composition and to start from previously prepared base materials. This proves to be of great advantage specifically when using the minerals of the apatite group since it is thus no longer necessary to start with components corresponding stoichiometrically to the apatite structure which then precipitates or separates spontaneously from the base glass. It is also possible in a predetermined manner to incorporate other apatites such as, for instance, chlorapatite $(Ca_5[Cl(PO_4)_3])$ and/or hydroxylapatite $(Ca_5[OH(PO_4)_3])$.

Furthermore, the sintering process of the present invention allows to use for synthesizing or producing the desired composite material well-crystallized apatites or, respectively, apatites of disturbed crystal structure such as they can be obtained, for instance, by precipitation.

According to an advantageous embodiment of the present invention, the sintering process proceeds in accordance with the following four process steps:

Step (a) The two starting materials A and B are ground, preferably jointly, for instance, in a ball mill, to a particle size preferably between about 200 μm. and about 500 μm.

Step (b) The resultant mixture of the starting materials A and B is finely comminuted to a particle size preferably between about 20 μm. and about 50 μm.

Step (c) The finely comminuted mixture of the starting materials A and B is compressed to form shaped bodies, preferably while simultaneously applying heat thereto. Such molding is effected at a pressure between about 50 atmospheres and about 1000 atmospheres and preferably between about 100 atmospheres and about 500 atmospheres.

Step (d) The compresses and molded mixture of the starting materials A and B is then sintered, for instance, in a muffle furnace. The sintering temperature is between about 500° C. and about 900° C. and preferably between about 500° C. and about 750° C. The sintering time is between about 10 minutes and about 300 minutes.

Thereby it can be of advantage to effect classification of the ground mixture of material, for instance, by means of a screen, after the first process step (a) and before the second finely comminuting step (b). Such classification step (a 1) has the advantage that the more coarsely ground starting materials A and B or their mixture are homogenized with respect to their size so that only particles of an advantageous predetermined, relatively uniform particle size are subjected to fine comminution in step (b). For instance, it may be advisable to eliminate all particles exceeding 300 μm. from the ground starting materials or their mixture before subjecting them to fine comminution in step (b).

It is also possible to subject the compressed mixture to a presintering step (c 1), preferably with simultaneous application of pressure, i.e., to a press-sintering step, following the third molding process step (c) and before the fourth sintering step (d).

According to another embodiment of the process of the present invention, animal or human bone or tooth ash is used as the first starting material A and a known glass of the following composition, in weight percent:
between about 20% and about 60% and preferably between about 30% and about 60% of silicon dioxide $SiO_2$;
between about 5% and about 40% and preferably between about 5% and about 20% of phosphorus pentoxide $P_2O_5$;
between about 2.7% and about 20% and preferably between about 3% and about 10% of sodium oxide $Na_2O$;
between about 0.4% and about 20% and preferably between about 3% and about 10% or potassium oxide $K_2O$;
between about 2.9% and about 30% and preferably between about 5% and about 20% of magnesium oxide MgO; and
between about 5% and about 40% and preferably between about 10% and about 30% of calcium oxide CaO is used as the second starting material B.

The glass ceramic material according to the present invention is produced from a mixture consisting substantially of silicon dioxide, $SiO_2$, sodium oxide, $Na_2O$, potassium oxide, $K_2O$, magnesium oxide, MgO, and a calcium phosphate. The amounts of the components in said mixture are such that a glass ceramic material of the oxide composition as given hereinabove, is produced.

Preferably the glass ceramic material of the above given composition is obtained by melting down a mixture essentially consisting, in weight percent, of
about 20% to about 60% of silicon dioxide, $SiO_2$,
about 2.7% to about 20% of sodium oxide, $Na_2O$,
about 0.4% to about 20% of potassium oxide, $K_2O$,
about 2.9% to about 30% of magnesium oxide, MgO,
about 5% to about 25% of calcium oxide CaO, and
about 10% to about 30% of calcium orthophosphate, $Ca_3(PO_4)_2$.

In place of bone or tooth ash, there can also be added artificial inorganic material substantially corresponding in its composition to the natural skeleton material as it is described, for instance, by ROBERT KLEMENT in the article of "Die anorganische Skelettsubstanz. Ihre Zusammensetzung, natuerliche und keunstliche Bildung" published in "Die Naturwissenschaften" vol. 26, No. 10, pages 145 to 152 (March 11, 1938), or mixtures of compounds of calcium, magnesium, sodium, and/or potassium cations and of phosphate and carbonate anions of the composition given in said article, i.e., inorganic hydroxylapatites of the following approximate composition:
between about 32.0% and about 36.0% of calcium Ca,
between about 44.0% and about 47.5% of phosphate $PO_4$,
between about 4.0% and about 5.7% of carbonate $CO_3$,
between about 0.25% and about 1.2% of magnesium Mg,
between about 0.35% and about 0.6% of sodium Na, and
between about 0.07% and about 0.25% of potassium K.

The first starting material A may also be composed of at least two of the following mineral components:
a natural or synthetic mineral of the apatite group;
a natural or synthetic mineral of the permutite group;
animal or human bone ash;
animal or human tooth ash.

These components are present in the mixture in any desired ratio, preferably in a ratio between about 95 : 5 and about 5 : 95 and more advantageously between about 65 : 35 and about 35 : 65, calculated for a sum total of the first starting material A of 100 parts by weight.

The second starting material B may be a mixture, preferably an oxidic mixture from which a glass having, for instance, the above-indicated composition can be melted in a known manner.

The second starting material B can also contain at least one radioactive compound, for instance, thorium oxide $ThO_2$ or at least one ray-absorbing and particularly one γ-ray-absorbing compound, for instance, lead oxide PbO or at least one compound which is capable of foam formation in the sintered material, for instance, a carbonate.

The ratio of the weight of the first starting material A to that of the second starting material B is between about 1 : 99 and about 99 : 1 and preferably between about 23 : 77 and about 75 : 25 calculated for a total quantity of the two starting materials of 100 parts by weight.

Pressing according to step (c) of the process of the present invention is carried out under a pressure between about 50 atmospheres and about 1000 atmospheres and at a temperature between about 50° C. and about 250° C. within a period of time between about 5 minutes and about 300 minutes. Preferably the pressure is between about 100 atmospheres and about 500 atmospheres at a temperature between 80° C. and about 120° C. and within a period of time between about 10 minutes and about 30 minutes.

Sintering according to step (d) is effected at a temperature between about 500° C. and about 750° C. within a period of time between about 10 minutes and about 100 minutes.

If a preliminary sintering step (c 1) is effected between the compressing step (c) and the sintering step (d), the temperature of said presintering step is between about 400° C. and about 800° C. and preferably between about 400° C. and about 600° C. while the presintering time amounts to between about 8 minutes and about 240 minutes and preferably between about 8 minutes and about 80 minutes.

It is, of course, understood that the temperature-time schedules as given hereinabove depend upon the specific composition of the respective starting materials A and B or their mixtures. Optimum conditions can readily be determined by a person skilled in this art by preliminary routine tests.

Producing the starting materials A or, respectively, B or mixtures of said starting materials A and B and thus synthesizing said mineral materials, for instance, precipitation of apatite crystallites of disturbed crystal lattice from aqueous solutions or, respectively, production of bone or tooth ash by burning bones or teeth, or respectively, melting down of a given glass composition as second starting material B does not in itself form an object of the present invention. The above indicated glass composition is, for instance, disclosed in the above mentioned U.S. Pat. No. 3,922,155, the disclosure of said patent being made part of the present application by reference. The mixing ratio of the first starting material mixture A is, as stated above, between the ratios of about 95 : 5 and about 5 : 95 and preferably between about 65 : 35 and about 35 : 65 calculated for a total material mixture of 100 parts by weight.

To the second starting material or mixture of materials B there can be added as further inorganic component foam-producing substances as they are conventionally used in the melting technique, such as alkaline earth metal or alkali metal carbonates, in quantities up to 10% of the total weighed-in portion of both starting materials A and B. Their readily volatile decomposition products escape at last partly during the sintering process and thus cause a certain foaming, i.e., an increase in volume of the final composite material as the result of the formation of gas bubbles. A composite material structured in this manner can be used in particular as filler, for instance, as filling material for long hollow bones and the like. Its porous isotropically loosened structure renders it especially useful as such hollow-space filling material.

Other inorganic additions to the starting mixture B are, for instance, compounds which contain lead ions. Composite materials obtained therewith make it possible to provide a locally precisely defined protective screening function in the living organism. For instance, implanted dorsal vertebrae which have been made by the process of this invention from a lead-doped composite material may serve to a certain extent as local radiation-protecting screen against corpuscular irradiation of the spinal cord. On the other hand, incorporation of thorium-containing ions in the composite material by the addition of thorium-containing compounds to the inorganic second starting material B is indicated when it is desired to implant in the human or animal organism a weak radioactive source of radiation which serves for a directed therapeutic or prophylactic treatment of certain organic anomalies.

The use of permutites permits a directed removal from or addition of ions into the organism. These additives which chemically are similar to the mineral group of the zeolites (see F. HELFERICH, "Ionenaustauscher," volume I, published by Verlag Chemie GmbH, Weinheim, 1959, pages 10–12) are known as ion exchangers due to their large-size crystal lattice structures which are permeated by long channels. Implanted composite materials containing permutite thus have the property of taking up in preferred fashion harmful ions present in the living organism, such as, for instance, lead or radioactive barium. Such composite materials can be implanted at a suitable site in the organism to serve, so to say, as biologically-physiologically active filters. When properly and selectively adjusted, they can either intercept and store harmful ions or, if desired, they can give off ions required by the organism, such as, for instance, calcium, magnesium, or potassium or they can exchange ions roaming in the organism by ions which can move relatively freely within the permutite space structure. Since it has been found that permutites themselves have an increased affinity for such ions which are harmful to the organism, the undetected supply or introduction, for instance, of radioactive ions would be recognizable at a very early stage by radiation monitoring.

The starting materials or mixtures of starting materials A and B can be mixed with each other — calculated for 100 parts by weight of the total amount of the mixture — in any ratio within the ratios of 1 : 99 and 99 : 1.

The resulting composite material produced according to the present invention which, due to the specific temperature-time sintering program employed, contains discrete crystallites, for instance, of apatite in the specifically composed matrix, has proved to be useful, as pointed out hereinabove, for prosthetic purposes, i.e., for replacing bones or teeth. The composite material of the present invention is especially suitable for this purpose not only because of the above-indicated advantages such as compatibility with the body, possibility of completely growing together with the bones present in the body, and others, but also because these materials can readily be worked mechanically. Such composite materials can be cast into molds, they can be subjected to plastic deformation and can be compressed, cut, blown, milled, sawed, filed, drilled, and the like.

For instance, the composite material according to the present invention can be used for replacing knee joints which have become stiff due to rheumatoid arthritis or the like. It is possible to restore to a large extent proper functioning of such knee joints.

The same result with respect to their functioning is achieved by replacing hip joints or the head of the femur by such composite materials.

Said composite material has also been used successfully for replacing teeth by implanting it in suitably shaped form into the jaw bone. Preferably the prosthesis is fastened to the jaw bone by means of screws, needles, clamps, or the like. It is also possible to provide the shaped composite material with a thread so that it can be threaded into the jaw bone. Or it can be shaped like a dowel and dowelled into the jaw bone.

A complicated bone fracture can be repaired by removing the damaged part of the bone and inserting in its place a correspondingly shaped replacement part. Such a replacement part usually grows together at the places of contact with the natural bone material within three to six weeks.

According to another embodiment of the present invention the composite material can be distributed in the form of a powder upon the surface of a suitably shaped article composed of a conventional bone replacing material, for instance, upon the surface of a bone shaped article of aluminum oxide or a metallic replacement part. The thus coated article is then subjected to a temperature treatment to cause sintering or fusing together of the powder coating and forming a porous sintered surface layer. Said layer retains the outstanding properties of the composite material and especially its biocompatibility and, as a result thereof, the thus refined aluminum oxide or metal bone replacement part can readily be implanted in the body.

The composite material of the present invention and articles made therefrom can also be provided with pigments or dyes dispersed therein for certain decorative purposes.

It is furthermore possible to optimize the parameters of solid-state body mechanics by purposeful incorporation in the manner of fiber-reinforced materials. Thus, for instance, the weight of the bone implant can be reduced by producing a compact tubular glass ceramic material and providing its cavity with the foamed composite material of the same composition. Care must be taken thereby, however, that the mechanical strength and stability properties of the resulting bone implant are not substantially reduced and impaired.

BRIEF DESCRIPTION OF THE DRAWING

The attached drawing illustrates diagrammatically in the form of a flow sheet the manner in which the process according to the present invention is carried out. As shown in the flow sheet the two starting materials A and B or mixtures thereof are subjected simultaneously or in rapid sequence to the individual process steps (a) and (b) and thereafter to process steps (c) and (d). Said process steps are carried out in known apparatus such as mills, presses, and furnaces under the above-described process conditions such as temperature, pressure, time, classifying of particle size, etc.

DESCRIPTION OF THE PREFERRED EMBODIMENT

The following example serves to illustrate the present invention without, however, limiting the same thereto.

EXAMPLE 20 g. of fluorapatite ($Ca_5[F(PO_4)_3]$) prepared by precipitation from aqueous solution and representing the first starting material and 34 g. of a ground glass of the following composition, in weight percent:
46.2% of silicon dioxide $SiO_2$,
25.5% of tricalciumphosphate $Ca_3(PO_4)_2$,
20.2% of calcium oxide CaO,
2.9% of magnesium oxide MgO,
4.8% of sodium oxide $Na_2O$, and
0.4% of potassium oxide $K_2O$
are intimately mixed with each other and the mixture is processed according to the present invention as follows:
Step (a): The mixture of starting materials A and B is ground to a particle size not exceeding 500 μm. and is classified by means of a screen into two different fractions, one of them having a particle size not exceeding 350 μm.
Step (b): The mixture of such particle size is finely comminuted to a powder of the particle size of about 30 μm.
Step (c): The powder mixture is then compressed under a pressure of about 300 atmospheres so as to form the desired shaped body while heating at about 100° C. for a period of time of 20 minutes.
Step (d): The compressed and molded body is sintered at atmospheric pressure and at a temperature of about 670° C. for a period of 100 minutes.

The resulting molded and sintered body is used as bone replacement material.

Of course, the composition of the starting materials A and B can be varied as described hereinabove. Due to the many possibilities of selecting starting materials A and B of varying composition, the conditions under which the process according to the present invention is carried out can also be varied within the limits indicated.

Heat can be supplied in the sintering step (d) and/or during the compression step (c) or on presintering by all technologically feasible means and in particular by induction heating, by heating by means of an electron beam, or by heating by means of a laser beam.

Of course, many changes and variations in the composition of the starting materials A and B, in the particle size of said starting materials as produced by grinding and comminuting, in the classification, compressing and molding, presintering, and sintering conditions, in the use of the resulting composite material in medico-engineering, for osteosynthesis and for other purposes may be made by those skilled in the art in accordance with the principles set forth herein and in the claims annexed hereto.

We claim:
1. A process for the production of a composite therapeutically useful as a prosthetic material for replacing bones and teeth of humans and animals, said process comprising the steps of:
(a) comminuting a mixture of about 20 parts fluorapatite $Ca_5[F(PO_4)_3]$ prepared by precipitation and about 34 parts glass composition consisting essentially in weight percent of:
between about 20% and about 60% of silicon oxide, $SiO_2$,
between about 5% and about 40% of phosphorus pentoxide, $P_2O_5$,
between about 2.7% and about 20% of sodium oxide, $Na_2O$,
between about 0.4% and about 20% of potassium oxide, $K_2O$,
between about 2.9% and about 30% of magnesium oxide, MgO,
and between about 5% and 40% of calcium oxide, CaO,
(b) classifying the ground mixture by means of a screen into two fractions of different particle size;
(c) finely comminuting the fraction of smaller particle size to about 30 μm;
(d) compressing and molding the finely comminuted mixture into a shaped body at a pressure of about 300 atmospheres while simultaneously subjecting the mixture to a heat treatment of about 100° C for a period of about 20 minutes; and

(e) sintering the compressed and molded shaped body at atmospheric pressure and at a temperature of about 670° C for a period of time of about 100 minutes whereby said glass composition is melted and said composite produced is characterized by discrete crystallites of said fluorapatite dispersed in a matrix of said glass.

2. The product produced by the process of claim 1.

* * * * *